United States Patent
Arai et al.

(10) Patent No.: US 12,083,226 B2
(45) Date of Patent: Sep. 10, 2024

(54) STABILIZER-CONTAINING SOLID DRUG FORMULATION

(71) Applicant: DAIICHI SANKYO COMPANY, LIMITED, Tokyo (JP)

(72) Inventors: Hiroaki Arai, Tokyo (JP); Shinji Yoshinaga, Tokyo (JP); Yurika Ozaki, Tokyo (JP)

(73) Assignee: DAIICHI SANKYO COMPANY, LIMITED, Tokyo (JP)

( * ) Notice: Subject to any disclaimer, the term of this patent is extended or adjusted under 35 U.S.C. 154(b) by 499 days.

(21) Appl. No.: 17/264,563

(22) PCT Filed: Jul. 29, 2019

(86) PCT No.: PCT/JP2019/029580
§ 371 (c)(1),
(2) Date: Jan. 29, 2021

(87) PCT Pub. No.: WO2020/027019
PCT Pub. Date: Feb. 6, 2020

(65) Prior Publication Data
US 2021/0330592 A1 Oct. 28, 2021

(30) Foreign Application Priority Data
Jul. 30, 2018 (JP) ................................. 2018-142885

(51) Int. Cl.
*A61K 9/20* (2006.01)
*A61K 9/28* (2006.01)
*A61K 31/195* (2006.01)

(52) U.S. Cl.
CPC .............. *A61K 9/2013* (2013.01); *A61K 9/28* (2013.01); *A61K 31/195* (2013.01)

(58) Field of Classification Search
CPC ....... A61K 9/2013; A61K 9/28; A61K 31/195
See application file for complete search history.

(56) References Cited

U.S. PATENT DOCUMENTS

| | | | |
|---|---|---|---|
| 5,032,390 A | 7/1991 | Iwaya et al. | |
| 5,304,381 A * | 4/1994 | Uesugi et al. | A61K 47/22 |
| | | | 424/484 |
| 6,054,482 A | 4/2000 | Augart et al. | |
| 7,351,429 B1 | 4/2008 | Ohyama et al. | |
| 7,794,748 B2 | 9/2010 | Sugihara et al. | |
| 7,947,738 B2 | 5/2011 | Shimada et al. | |
| 8,324,425 B2 | 12/2012 | Kitagawa et al. | |
| 8,895,141 B2 | 11/2014 | Satomi et al. | |
| 9,675,570 B2 * | 6/2017 | Tajiri et al. | A61K 31/195 |
| 2001/0004637 A1 | 6/2001 | Hanamura et al. | |
| 2005/0026981 A1 | 2/2005 | Sugihara et al. | |
| 2007/0099986 A1 | 5/2007 | Ishichi et al. | |
| 2009/0041843 A1 | 2/2009 | Kozaki et al. | |
| 2010/0062063 A1 | 3/2010 | Umejima et al. | |
| 2010/0249229 A1 | 9/2010 | Shimada et al. | |
| 2011/0135927 A1 | 6/2011 | Satomi et al. | |
| 2011/0305758 A1 | 12/2011 | Matono et al. | |
| 2012/0071685 A1 | 3/2012 | Kitagawa et al. | |
| 2012/0156261 A1 | 6/2012 | Fugiwara et al. | |
| 2012/0219637 A1 | 8/2012 | Aniket et al. | |
| 2012/0294947 A1 | 11/2012 | Kuninobu et al. | |
| 2013/0243859 A1 | 9/2013 | Ishii et al. | |
| 2013/0245288 A1 | 9/2013 | Kimura et al. | |
| 2013/0309313 A1 | 11/2013 | Gareau et al. | |
| 2013/0345444 A1 | 12/2013 | Yamano et al. | |
| 2014/0024699 A1 | 1/2014 | Kaelin, Jr. et al. | |
| 2014/0030209 A1 | 1/2014 | Furuta et al. | |
| 2015/0079166 A1 | 3/2015 | Tajiri et al. | |
| 2015/0231101 A1 * | 8/2015 | Lindenblatt | A61K 9/1658 |
| | | | 424/490 |
| 2016/0361261 A1 * | 12/2016 | Carpanzano et al. | ... A61K 9/16 |
| 2018/0042874 A1 * | 2/2018 | Tajiri et al. | A61K 31/195 |

(Continued)

FOREIGN PATENT DOCUMENTS

| | | |
|---|---|---|
| CN | 1938014 A | 3/2007 |
| CN | 100379416 C | 4/2008 |

(Continued)

OTHER PUBLICATIONS

Chen-Feng et al., "Study of Aromatic Nano-TiO2 Modified Acrylic-Polyurethane Composites," *Chemical Materials for Construction*, (2007), 23(2):30-32.

Cutrignelli et al., "Comparative effects of some hydrophilic excipients on the rate of gabapenting and baclofen lactamization in lyophilized formulations," *International Journal of Pharmaceutics*, (2007), 332:98-106.

(Continued)

*Primary Examiner* — Robert A Wax
*Assistant Examiner* — Andre Mach
(74) *Attorney, Agent, or Firm* — Dorsey & Whitney LLP

(57) ABSTRACT

An object of the present invention is to provide a solid drug formulation having excellent stability. The solution according to the present invention is a solid drug formulation containing:

a compound having formula (I):

[Formula 1]

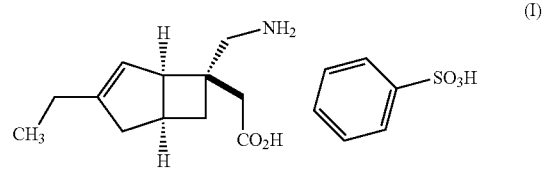

(i) D-mannitol; (ii) carmellose calcium; (iii) citric acid hydrate or the like; and (iv) α-tocopherol.

9 Claims, No Drawings

(56) References Cited

U.S. PATENT DOCUMENTS

| | | | |
|---|---|---|---|
| 2018/0042878 A1* | 2/2018 | Tajiri | A61K 9/2013 |
| 2018/0243223 A1 | 8/2018 | Tajiri et al. | |

FOREIGN PATENT DOCUMENTS

| | | | | |
|---|---|---|---|---|
| CN | 101878193 | A | 11/2010 | |
| CN | 101732290 | | 8/2013 | |
| CN | 104334169 | A | 2/2015 | |
| EP | 0387655 | A | 9/1990 | |
| EP | 1 205 190 | A1 | 5/2002 | |
| EP | 1 245 232 | A1 | 10/2002 | |
| EP | 2 826 477 | A1 | 1/2015 | |
| EP | 3 272 346 | A1 | 1/2018 | |
| GB | 3 272 346 | A1 * | 1/2018 | A61K 31/195 |
| JP | 2-247126 | A | 10/1990 | |
| JP | 9-169642 | A | 6/1997 | |
| JP | 11-189547 | A | 7/1999 | |
| JP | 2001-064177 | A | 3/2001 | |
| JP | 2003-104887 | A | 4/2003 | |
| JP | 2005-263790 | A | 9/2005 | |
| JP | 2007-131542 | A | 5/2007 | |
| JP | 2009-275041 | A | 11/2009 | |
| JP | 4479974 | B2 | 6/2010 | |
| JP | 2010-241796 | A | 10/2010 | |
| JP | 2013-35797 | A | 2/2013 | |
| WO | 01/12193 | A1 | 2/2001 | |
| WO | 01/34147 | A1 | 5/2001 | |
| WO | WO 2004/017947 | A1 * | 3/2004 | A61K 9/16 |
| WO | 2006/056874 | A1 | 6/2006 | |
| WO | 2007/052592 | A1 | 5/2007 | |
| WO | 2009/041453 | A1 | 4/2009 | |
| WO | 2010/021300 | A1 | 2/2010 | |
| WO | 2010/087462 | A1 | 8/2010 | |
| WO | 2013/021660 | A1 | 2/2013 | |
| WO | 2014/163132 | A1 | 10/2014 | |
| WO | 2016/148263 | A1 | 9/2016 | |
| WO | 2016/148264 | A1 | 9/2016 | |
| WO | WO 2018/003980 | A1 | 1/2018 | |

OTHER PUBLICATIONS

Ferin et al., "Biological Effects and Toxicity Assessment of Titanium Dioxides: Anastase and Rutile," *American Industrial Hygiene Association Journal*, (2010), 46(2):69-72, abstract published online at https://www.tandfonline.com/doi/pdf/10.1080/15298668591394 9? need Access=true.

Hashida, "The Design and Evaluation of Oral Medications," Published Feb. 10, 1995, by Yakugyo Jiho Co., Tokyo, Japan, pp. 50-51.

Jing, "Application Directory of Pharmaceutical Excipients," China Medical Science Press, Aug. 31, 2011, pp. 187-189.

Tsuda (Ed.), "Pharmaceutical Engineering, Course X, Fundamentals of Pharmaceutical Development," Published Mar. 1, 1971, by Chijin Shoka Co., Ltd., Tokyo, Japan, pp. 161-162, 167, 170-171, and 179.

Yakuji Nippo Limited, "Pharmaceutical Excipients Dictionary 2007," International Pharmaceutical Excipients Council Japan, 50 pages, including translation into English.

Zongmao, "Production and Application of a Pharmaceutical Excipient-Thin Film Coating," China Medical Science Press, May 31, 2014, pp. 53-61.

English translation of International Search Report issued Apr. 28, 2014, in PCT Application No. PCT/JP2014/059812, 2 pp.

English Translation of International Search Report issued Jun. 7, 2016, for PCT Application No. PCT/JP2016/058608, 3 pages.

English Translation of Written Opinion issued Jun. 7, 2016, for PCT Application No. PCT/JP2016/058608, 7 pages.

English Translation of International Search Report issued Jun. 7, 2016, in PCT Application No. PCT/JP2016/058607, 3 pages.

English Translation of Written Opinion issued Jun. 7, 2016, in PCT Application No. PCT/JP2016/058607, 6 pages.

English Translation of International Search Report mailed Sep. 3, 2019, for PCT Application No. PCT/JP2019/029580, 2 pages.

English Translation of Written Opinion mailed Sep. 3, 2019, for PCT Application No. PCT/JP2019/029580, 6 pages.

\* cited by examiner

STABILIZER-CONTAINING SOLID DRUG FORMULATION

This application is a national stage application under 35 U.S.C. § 371 of International Application No. PCT/JP2019/029580, filed Jul. 29, 2019, entitled "STABILIZER-CONTAINING SOLID DRUG FORMULATION," which claims priority to Japanese Patent Application No. 2018-142885, filed Jul. 30, 2018.

TECHNICAL FIELD

The present invention relates to: a solid drug formulation containing citric acid anhydride or citric acid hydrate and α-tocopherol in combination as a stabilizer, and further containing [(1R,5S,6S)-6-(aminomethyl)-3-ethylbicyclo[3.2.0]hept-3-en-6-yl]acetic acid monobenzenesulfonate (hereinafter, occasionally referred to as "compound (I)"); and a method for producing the solid drug formulation.

The present invention also relates to a method for stabilizing compound (I) in a solid drug formulation containing compound (I) by adding citric acid anhydride or citric acid hydrate and α-tocopherol in combination as a stabilizer to the solid drug formulation containing compound (I).

BACKGROUND ART

Compound (I) represented by the following structural formula:

[Formula 1]

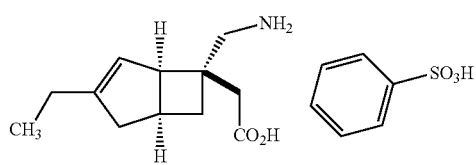

is disclosed in U.S. Pat. No. 7,947,738 (Patent Literature 1), and expected to be applicable to analgesics, other drugs for the central nervous system, other drugs for the peripheral nervous system, therapeutic drugs for skeletal muscle diseases, and so forth, because of its excellent activity as an $α_2S$ ligand. Pharmaceutical compositions containing compound (I) are disclosed in U.S. Pat. No. 9,675,570, US2018-0042878, and EP3272346 (Patent Literatures 2 to 4).

CITATION LIST

Patent Literature

Patent Literature 1: U.S. Pat. No. 7,947,738
Patent Literature 2: U.S. Pat. No. 9,675,570
Patent Literature 3: US2018-0042878
Patent Literature 4: EP3272346

SUMMARY OF INVENTION

Technical Problem

In the course of diligently continued research in search of a solid drug formulation having superior stability, from solid drug formulations containing compound (I), the present inventors have found that use of citric acid anhydride or citric acid hydrate and α-tocopherol in combination, in particular, inclusion of these components with specific contents and/or content ratios, provides a particularly excellent stabilizing effect, thus completing the present invention.

Solution to Problem

Specifically, based on the finding, as described later, that use of compound (I) represented by the following structural formula:

[Formula 2]

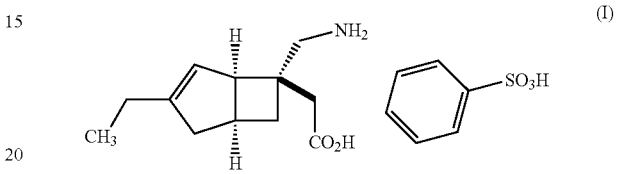

in combination with citric acid anhydride or citric acid hydrate and α-tocopherol, in particular, inclusion of these components with specific contents and/or content ratios provides a particularly excellent stabilizing effect, the present invention relates to: a solid drug formulation (preferably a tablet) containing a combination of compound (I), citric acid anhydride or citric acid hydrate, and α-tocopherol; and a method for producing such a stabilized solid drug formulation.

Preferred embodiments of the present invention are as shown in the following.

[1] A drug tablet containing:
[(1R,5S, 6S)-6-(aminomethyl)-3-ethylbicyclo[3.2.0]hept-3-en-6-yl]acetic acid monobenzenesulfonate as a compound having formula (I):

[Formula 3]

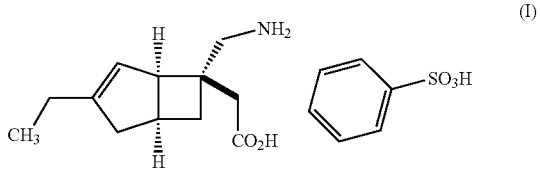

(i) D-mannitol;
(ii) carmellose calcium;
(iii) citric acid anhydride or citric acid hydrate, wherein the content of citric acid anhydride or citric acid hydrate is 0.01 to 10% by weight, in terms of citric acid hydrate, based on the total weight of a plain tablet of the drug tablet; and
(iv) α-tocopherol, wherein the content of α-tocopherol is 0.001 to 1.0% by weight based on the total weight of the plain tablet.

[2] The tablet according to [1], wherein the content of citric acid anhydride or citric acid hydrate is 1.0 to 5.0% by weight, in terms of citric acid hydrate, based on the total weight of the plain tablet.

[3] The tablet according to [1], wherein the content of citric acid anhydride or citric acid hydrate is 1.125 to 2.9% by weight, in terms of citric acid hydrate, based on the total weight of the plain tablet.

[4] The tablet according to any one of [1] to [3], wherein the content of α-tocopherol is 0.005 to 1.0% by weight based on the total weight of the plain tablet.

[5] The tablet according to any one of [1] to [3], wherein the content of α-tocopherol is 0.005 to 0.5% by weight based on the total weight of the plain tablet.

[6] The tablet according to any one of [1] to [3], wherein the content of α-tocopherol is 0.05 to 0.5% by weight based on the total weight of the plain tablet.

[7] The tablet according to any one of [1] to [6], wherein the content of the compound having formula (I) is 1.0 to 5.0% by weight, in terms of the free form of the compound, based on the total weight of the plain tablet.

[8] The tablet according to any one of [1] to [7], wherein the average particle size of D-mannitol is 120 μm or smaller, and the content of D-mannitol is 75 to 85% by weight based on the total weight of the plain tablet.

[9] The tablet according to any one of [1] to [8], wherein the content of carmellose calcium is 5 to 15% by weight based on the total weight of the plain tablet.

[10] The tablet according to any one of [1] to [9], further containing magnesium stearate.

[11] The tablet according to [10], wherein the content of magnesium stearate is 1 to 3% by weight based on the total weight of the plain tablet.

[12] The tablet according to any one of [1] to [11], further containing magnesium aluminometasilicate and microcrystalline cellulose.

[13] The tablet according to any one of [1] to [12], wherein the tablet is a film-coated tablet.

Advantageous Effects of Invention

Based on the finding that use of compound (I) in combination with citric acid anhydride or citric acid hydrate and α-tocopherol, in particular, inclusion of these components with specific contents and/or content ratios, provides a particularly excellent stabilizing effect, the present invention provides: a solid drug formulation (preferably a tablet) containing a combination of compound (I), citric acid anhydride or citric acid hydrate, and α-tocopherol; and a method for producing such a stabilized solid drug formulation.

DESCRIPTION OF EMBODIMENTS (Components and Preferred Contents)

Compound (I) used as an active ingredient in the present invention preferably has an average particle size of 60 μm (more preferably 40 μm) or smaller.

The term "average particle size" in the present invention refers to the particle size at a cumulative value of 50% in a particle size distribution determined by using a laser diffraction/scattering method.

The content of compound (I) used in the present invention is preferably 0.5 to 40% by weight, more preferably 0.5 to 25% by weight, and particularly preferably 0.5 to 10% by weight (further particularly preferably 1.0 to 5.0% by weight), in terms of the free form, based on the total weight of the plain tablet.

Diluents in the present invention refer to components that are described in common reference books on formulations (e.g., "Handbook of PHARMACEUTICAL EXCIPIENTS Fifth Edition", Yakuji Nippo, Limited, Feb. 28, 2007) and added for the purpose of providing a certain size or concentration in the formulation of tablets or the like. Examples of diluents include ammonium alginate, calcium carbonate, anhydrous dibasic calcium phosphate, dibasic calcium phosphate dihydrate, tribasic calcium phosphate, calcium sulfate, microcrystalline cellulose, powdered cellulose, silicified microcrystalline cellulose, cellulose acetate, dextrate, dextrin, dextrol, erythritol, ethyl cellulose, fructose, glycerol palmitostearate, isomalt, kaolin, lactitol, lactose monohydrate, anhydrous lactose, spray-dried lactose, magnesium carbonate, magnesium oxide, maltodextrin, maltose, D-mannitol, polymethacrylate, simethicone, sodium chloride, sorbitol, starch, pregelatinized starch, white soft sugar, compressible sugar, confectionery sugar, sucrose spheres, sulfobutyl ether β-cyclodextrin, talc, trehalose, and xylitol, and a particularly preferred example is D-mannitol.

The content of D-mannitol used in the present invention is preferably 50 to 90% by weight and more preferably 75 to 85% by weight based on the total weight of the plain tablet.

It is desired that D-mannitol used in the present invention has an average particle size smaller than 150 μm, and the average particle size of D-mannitol is preferably 120 μm or smaller.

Disintegrants in the present invention refer to components that are described in common reference books on formulations (e.g., "Handbook of PHARMACEUTICAL EXCIPIENTS Fifth Edition", Yakuji Nippo, Limited, Feb. 28, 2007) and added for the purpose of disintegrating tablets, for example, through swelling due to absorption of moisture in the body to facilitate release of active ingredients. Examples of disintegrants include alginic acid, calcium alginate, carboxymethylcellulose calcium (carmellose calcium), carboxymethylcellulose sodium, microcrystalline cellulose, powdered cellulose, chitosan, colloidal silicon dioxide, croscarmellose sodium, crospovidone, guar gum, low-substituted hydroxypropylcellulose, hydroxypropylstarch, aluminum magnesium silicate methylcellulose, polacrilin potassium, povidone, sodium alginate, sodium starch glycolate, starch, and pregelatinized starch, and a particularly preferred example is carmellose calcium.

The content of carmellose calcium used in the present invention is preferably 2 to 20% by weight and preferably 5 to 15% by weight based on the total weight of the plain tablet.

The content of magnesium stearate used in the present invention is preferably 0.5 to 5% by weight and more preferably 1 to 3% by weight based on the total weight of the plain tablet.

Citric acid anhydride or citric acid hydrate and α-tocopherol used in the present invention have the function of a stabilizer.

The content of citric acid anhydride or citric acid hydrate in the present invention is preferably 0.01 to 10% by weight, more preferably 1.0 to 5.0% by weight, even more preferably 1.125 to 2.9% by weight, and particularly preferably 1.5 to 2.9% by weight, in terms of citric acid hydrate, based on the total weight of the plain tablet.

The content of α-tocopherol in the present invention is preferably 0.001 to 1.0% by weight, more preferably 0.005 to 1.0% by weight, even more preferably 0.005 to 0.5% by weight, and particularly preferably 0.05 to 0.5% by weight based on the total weight of the plain tablet.

In the present invention, diluents, disintegrants, binders, fluidizers, lubricants, coloring agents, brightening agents, and so forth, may be further used as optional components commonly used in formulation, unless the advantageous effects of the present invention are deteriorated.

In embodiments of the present invention as a tablet, a preferred combination of contents of components based on the total weight of the plain tablet is as follows.

Compound (I) (in terms of the free form): 0.5 to 10% by weight
D-Mannitol: 50 to 90% by weight (average particle size is smaller than 150 μm)
Carmellose calcium: 2 to 20% by weight
Magnesium stearate: 0.5 to 5% by weight
Citric acid hydrate: 1.0 to 5.0% by weight
α-Tocopherol: 0.005 to 1.0% by weight
A more preferred combination is as follows.
Compound (I) (in terms of the free form): 1.0 to 5.0% by weight
D-Mannitol: 75 to 85% by weight (average particle size is 120 μm or smaller)
Carmellose calcium: 5 to 15% by weight
Magnesium stearate: 1 to 3% by weight
Citric acid hydrate: 1.5 to 2.9% by weight
α-Tocopherol: 0.05 to 0.5% by weight
An even more preferred combination further includes 0.15 to 0.3% by weight of magnesium aluminometasilicate and/or 0.9 to 4.5% by weight of microcrystalline cellulose.

(Method for Producing Solid Formulation)

The solid formulation of the present invention is obtained as a tablet, a coated tablet, or the like, by sequentially performing:
(1) a step of mixing a powder of compound (I) as an active ingredient with a diluent and/or disintegrant or the like, mixing the resultant with a stabilizer triturated and mixed in advance, as necessary, with a diluent and/or disintegrant, and further adding an aid (e.g., a lubricant) needed for formulation thereto;
(2) a tableting step of compressing the resulting particulate powder with a tablet press;
(3) a coating step of coating the surface of the resulting tablet, as necessary; and so forth.

Examples of methods for producing the solid formulation include:
(1) direct tableting, in which the active ingredient and excipients are mixed, and the mixture is directly subjected to compression molding with a tablet press;
(2) semi-direct tableting, in which the excipients are formed into granules, the active ingredient is mixed therewith, and the mixture is subjected to compression molding with a tablet press;
(3) dry granule compression, in which the active ingredient and excipients are granulated into granules with a dry method, a lubricant or the like is then added thereto, and the resultant is subjected to compression molding; and
(4) wet granule compression, in which the active ingredient and excipients are granulated into granules with a wet method, a lubricant or the like is then added thereto, and the resultant is subjected to compression molding.

For granulation, means of fluidized granulation, high-shear granulation, melting granulation, and so forth may be used.

Preferred in the present invention is such a method that a part of the excipients is granulated, without granulating a powder of the active ingredient, and a mix powder of them is directly tableted to prepare a tablet.

An exemplary method for producing the tablet of the present invention is as described in the following.

Compound (I) as an active ingredient is pulverized to give a uniform particle size, a diluent and/or disintegrant are/is added thereto and mixed together. Further, a triturated mix powder of a stabilizer to which a diluent and/or disintegrant have/has been added in advance, as necessary, is prepared. Thereafter, a mixture of them is sieved through a particle size regulator, a lubricant is then added thereto and further mixed together, and the resultant is then tableted with a tablet press, giving a plain tablet.

The resulting plain tablet is applied to a coater to produce a film-coated tablet.

The present invention will be described in more detail with reference to Examples; however, the Examples in the following are shown for describing the present invention, and the present invention should not be interpreted as being limited to the Examples.

EXAMPLES (Examples 1 to 6) Examination of Stabilizing Effect for Cases with Blending One Stabilizer and Blending Two Stabilizers (1) Example 1

(Trituration and Mixing)

A premix powder was prepared by sufficiently mixing 9.4 g of dl-α-tocopherol and 62.6 g of carmellose calcium with a mortar. In a polyethylene bag, 70.3 g of the premix powder and 244.7 g of D-mannitol were mixed together, and the mixture was sieved with a 500-μm mesh to produce a triturated mix powder of dl-α-tocopherol.

(Mixing/Sieving)

Compound (I), D-mannitol, citric acid hydrate, and the triturated mix powder of dl-α-tocopherol were weighed to reach blend ratios shown in Table 1, and mixed by using a V-blender (2 L) at a rotational frequency of 39 rpm for 5 minutes.

Sieving was performed with a Comil (U-5, φ1.143, QUADRO) at 600 rpm to produce a sieved powder.

Subsequently, magnesium stearate was weighed to reach a blend ratio shown in Table 1 and added to the sieved powder, and the resultant was mixed by using a V-blender (2 L) at a rotational frequency of 39 rpm for 5 minutes.

(Tableting)

Molding was performed by using a tablet press (Vela5, KIKUSUI SEISAKUSHO LTD.) at a tableting pressure of approximately 7.5 kN with setting the tablet mass to 100 mg, providing a plain tablet (containing 2.5% by weight of compound (I) as a weight ratio in terms of the free form to the plain tablet, an oblong tablet, 8.4×4.4 mm).

(Coating)

OPADRY (R) (herein, a mixture of hypromellose, talc, titanium oxide, ferric oxide, and yellow ferric oxide) was dispersed in purified water (12.5 w/w %) by using a stirrer (MAZELA Z, TOKYO RIKAKIKAI CO, LTD.) to produce a coating solution.

The plain tablet was coated by using a coater (HI-COATER FZ20, Freund Corporation) with an air supply temperature of 75° C., an air supply rate of 0.6 m$^3$/min, a spraying rate of approximately 3.5 g/min, a pan rotation frequency of 25 rpm, and an air exhaust temperature of approximately 58° C. at the end of drying, giving a coated tablet.

(2) Preparation of Coated Tablets of Examples 2 to 4

Coated tablets of Examples 2 to 4 were additionally prepared by using the preparation method in Example 1 with components and contents thereof shown in Table 1.

(3) Example 5

(Trituration and Mixing)

A premix powder was prepared by sufficiently mixing 17 g of dl-α-tocopherol and 42.5 g of carmellose calcium with a mortar. By using a high-speed mixer (LFS-GS-1J, EARTHTECHNICA CO., LTD.), 56.0 g of the premix powder and 280.0 g of carmellose calcium were mixed together at an agitator rotation frequency of 310 rpm and a chopper rotation frequency of 3000 rpm for 10 minutes to produce a triturated mix powder of dl-α-tocopherol.

(Mixing/Sieving)

Compound (I), D-mannitol, citric acid hydrate, and the triturated mix powder of dl-α-tocopherol were weighed to reach blend ratios shown in Table 1, and mixed by using a V-blender (2 L) at a rotational frequency of 39 rpm for 10 minutes.

Sieving was performed with a Comil (QC-197S, φ1.143, QUADRO) at 600 rpm to produce a sieved powder.

Subsequently, magnesium stearate was weighed to reach a blend ratio shown in Table 1 and added to the sieved powder, and the resultant was mixed by using a V-blender (2 L) at a rotational frequency of 39 rpm for 5 minutes.

(Tableting)

Molding was performed by using a tablet press (Vela5, KIKUSUI SEISAKUSHO LTD.) at a tableting pressure of approximately 10 kN with setting the tablet mass to 200 mg, providing a plain tablet (containing 2.5% by weight of compound (I) as a weight ratio in terms of the free form to the plain tablet, an oblong tablet, 10.6×5.6 mm).

(Coating)

OPADRY (R) was dispersed in purified water (12.5 w/w %) by using a stirrer (MAZELA Z, TOKYO RIKAKIKAI CO, LTD.) to produce a coating solution.

The plain tablet was coated by using a coater (HI-COATER LABO 30, Freund Corporation) with an air supply temperature of 70° C., an air supply rate of 0.8 m³/min, a spraying rate of approximately 8 g/min, a pan rotation frequency of 20 rpm, and an air exhaust temperature of approximately 60° C. at the end of drying, giving a coated tablet.

(3) Example 6

A coated tablet of Example 6 was additionally prepared by using the preparation method in Example 5 with components and contents thereof shown in Table 1.

(5) Comparative Example 1

(Mixing/Sieving)

Compound (I), D-mannitol, and carmellose calcium were weighed to reach blend ratios shown in Table 1, and mixed by using a V-blender (2 L) at a rotational frequency of 39 rpm for 5 minutes.

Sieving was performed with a Comil (U-5, φ1.143, QUADRO) at 600 rpm to produce a sieved powder.

Subsequently, magnesium stearate was weighed to reach a blend ratio shown in Table 1 and added to the sieved powder, and the resultant was mixed by using a V-blender (2 L) at a rotational frequency of 39 rpm for 5 minutes.

(Tableting)

Molding was performed by using a tablet press (Vela5, KIKUSUI SEISAKUSHO LTD.) at a tableting pressure of approximately 7.5 kN with setting the tablet mass to 100 mg, providing a plain tablet (containing 2.5% by weight of compound (I) as a weight ratio in terms of the free form to the plain tablet, an oblong tablet, 8.4×4.4 mm).

(Coating)

OPADRY (R) was dispersed in purified water (12.5 w/w %) by using a stirrer (MAZELA Z, TOKYO RIKAKIKAI CO, LTD.) to produce a coating solution.

The plain tablet was coated by using a coater (HI-COATER FZ20, Freund Corporation) with an air supply temperature of 75° C., an air supply rate of 0.6 m³/min, a spraying rate of approximately 3.5 g/min, a pan rotation frequency of 25 rpm, and an air exhaust temperature of approximately 58° C. at the end of drying, giving a coated tablet.

TABLE 1

| Components | Example 1 | Example 2 | Example 3 | Example 4 | Example 5 | Example 6 | Comparative Example 1 |
|---|---|---|---|---|---|---|---|
| Compound (I) | 4.39 | 4.39 | 4.39 | 4.39 | 4.39 | 4.39 | 4.39 |
| (as the free form) | (2.5) | (2.5) | (2.5) | (2.5) | (2.5) | (2.5) | (2.5) |
| D-Mannitol (Parteck M100, Merck KGaA) | 82.11 | 80.61 | 82.11 | 80.61 | 80.61 | 80.61 | 83.61 |
| Carmellose calcium (E.C.G-505, GOTOKU CHEMICAL COMPANY, LTD.) | 10 | 10 | 10 | 10 | 10 | 10 | 10 |
| dl-α-Tocopherol (MITSUBISHI-CHEMICAL FOODS CORPORATION) | 1.5 | 3 | — | — | 1 | 0.5 | — |
| Citric acid hydrate (Merck KGaA) | — | — | 1.5 | 3 | 2 | 2.5 | — |
| Magnesium stearate (common, Taihei Chemical Industrial Co., Ltd.) | 2 | 2 | 2 | 2 | 2 | 2 | 2 |
| Total in plain tablet | 100 | 100 | 100 | 100 | 100 | 100 | 100 |
| OPADRY (R) | 5 | 5 | 5 | 5 | 5 | 5 | 5 |
| Total | 105 | 105 | 105 | 105 | 105 | 105 | 105 |

(6) Evaluation Method and Results

The tablets of Examples 1 to 6 and Comparative Example 1 were left to stand under open conditions of 25° C./75% RH/12 weeks, and thereafter decomposition product A and decomposition product B, which were main decomposition products, were examined through measurement with UHPLC (1290 Infinity, Agilent Technologies).

(Analysis Conditions for UHPLC)
  Measurement wavelength: 215 nm
  Column: Sunshell C18 (2.1 mm ID×100 mm, 2.6 μm, produced by ChromaNik Technologies Inc.)
  Guard column: SecurityGuard ULTRA C18 (2.1 mm ID, produced by Phenomenex Inc.)
  Clean-up column: Ghost Trap DS (7.6 mm ID×30 mm, produced by Shimadzu Corporation)
  Column temperature: 45° C.
  Mobile phase A: 0.01 mol/L diammonium hydrogen phosphate buffer (pH 6.2)
  Mobile phase B: mixed solution of methanol/acetonitrile/0.01 mol/L diammonium hydrogen phosphate buffer (pH 6.2) (9:3:4)
  Analysis time: 35 minutes
  Injection volume: 3 μL
  Sample cooler temperature: constant temperature around 6° C.

(Relative retention time of decomposition product A and decomposition product B to retention time of compound (I))
  Decomposition product A: maximum value around 0.3
  Decomposition product B: 2.0 to 2.1 decomposition product B was smaller for the coated tablets with use of only citric acid hydrate as a stabilizer (Examples 3 and 4) than for the coated tablet without use of a stabilizer (Comparative Example 1).

These results reveal that dl-α-tocopherol primarily prevents the formation of decomposition product A and citric acid hydrate primarily prevents the formation of decomposition product B, and addition of a large quantity of dl-α-tocopherol promotes the formation of decomposition product B. As a reference level of 0.2% or less was applied to formation ratios of the decomposition products with reference to the statement "Identification Threshold (threshold for requirement of structural identification of impurities): 0.2%" in "Revision of Guidelines on Impurities in New Drug Products (PMSB/ELD Notification No. 0624001, dated Jun. 24, 2003)" (https://www.pmda.go.jp/files/000156811.pdf), the formation ratios of the decomposition products did not simultaneously clear the reference level in any of Examples 1 to 4 and Comparative Example 1.

On the other hand, both the formation ratio of decomposition product A and that of decomposition product B for the coated tablets with use of dl-α-tocopherol and citric acid hydrate as a stabilizer (Examples 5 and 6) were lower than those for the coated tablet without use of a stabilizer (Comparative Example 1). In particular, the formation ratios of the decomposition products for the case with blending 0.5% of dl-α-tocopherol and 2.5% of citric acid hydrate (Example 6) were both below the applied reference level, 0.2%.

These results reveal that addition of both of dl-α-tocopherol and citric acid hydrate in an appropriate range successfully reduces the formation of the decomposition products.

TABLE 2

|  | Example 1 | Example 2 | Example 3 | Example 4 | Example 5 | Example 6 | Comparative Example 1 |
|---|---|---|---|---|---|---|---|
| dl-α-Tocopherol (% by weight) | 1.5 | 3 | 0 | 0 | 1 | 0.5 | — |
| Citric acid hydrate (% by weight) | 0 | 0 | 1.5 | 3 | 2 | 2.5 | — |
| Decomposition product A (%) under open conditions of 25° C./75% RH/12 weeks | 0.08 | 0.08 | 0.15 | 0.26 | 0.08 | 0.12 | 1.10 |
| Decomposition product B (%) under open conditions of 25° C./75% RH/12 weeks | 1.07 | 1.40 | 0.22 | 0.13 | 0.28 | 0.19 | 0.42 |

Table 2 shows the results (amounts of decomposition product A and decomposition product B, % (calculated from peak area ratios)).

The amount of decomposition product A was smaller for the coated tablets with use of dl-α-tocopherol or citric acid hydrate as a stabilizer (Examples 1 to 4) than for the coated tablet without use of a stabilizer (Comparative Example 1). The formation ratio of decomposition product A for the cases with use of only dl-α-tocopherol (Examples 1 and 2) was approximately ½ or less of that for the cases with use of only citric acid hydrate (Examples 3 and 4). However, the amount of decomposition product B was larger for the coated tablets with use of only dl-α-tocopherol (Examples 1 and 2) than for the coated tablet without use of a stabilizer (Comparative Example 1). By contrast, the amount of (Examples 7 to 13) Examination of Stabilizing Effect with Different Blend Ratios of Stabilizer (1) Example 7

(Trituration and Mixing)

By using a high-speed mixing granulator (VG-5L, Powrex Corporation), 80.0 g of dl-α-tocopherol and 720.0 g of microcrystalline cellulose were mixed together at an agitator rotation frequency of 280 rpm and a chopper rotation frequency of 3000 rpm for 5 minutes to produce a triturated mix powder of dl-α-tocopherol.

(Mixing/Sieving)

Compound (I), D-mannitol, carmellose calcium, citric acid hydrate, the triturated mix powder of dl-α-tocopherol, and magnesium aluminometasilicate were weighed to reach blend ratios shown in Table 3, and mixed by using a V-blender (5 L) at a rotational frequency of 34 rpm for 10 minutes.

Sieving was performed with a Comil (U-5, φ1.143, QUADRO) at 1560 rpm to produce a sieved powder.

Subsequently, magnesium stearate was weighed to reach a blend ratio shown in Table 3 and added to the sieved powder, and the resultant was mixed by using a V-blender (5 L) at a rotational frequency of 34 rpm for 7 minutes.
(Tableting)

Molding was performed by using a tablet press (Vela5, KIKUSUI SEISAKUSHO LTD.) at a tableting pressure of approximately 9 kN with setting the tablet mass to 100 mg, providing a plain tablet (containing 2.5% by weight of compound (I) as a weight ratio in terms of the free form to the plain tablet, an oblong tablet, 8.4×4.4 mm).
(Coating)

OPADRY (R) was dispersed in purified water (12.5 w/w %) by using a stirrer (MAZELA Z, TOKYO RIKAKIKAI CO, LTD.) to produce a coating solution.

The plain tablet was coated by using a coater (HI-COATER LABO 30, Freund Corporation) with an air supply temperature of 70° C., an air supply rate of 0.8 m$^3$/min, a spraying rate of approximately 8 g/min, a pan rotation frequency of 20 rpm, and an air exhaust temperature of approximately 60° C. at the end of drying, giving a coated tablet.

(2) Examples 8 to 11

(Trituration and Mixing)

By using a high-speed mixing granulator (VG-5L, Powrex Corporation), 80.0 g of dl-α-tocopherol and 720.0 g of microcrystalline cellulose were mixed together at an agitator rotation frequency of 280 rpm and a chopper rotation frequency of 3000 rpm for 5 minutes to produce a triturated mix powder of dl-α-tocopherol.
(Mixing/Sieving)

Compound (I), D-mannitol, carmellose calcium, carmellose, citric acid hydrate, magnesium aluminometasilicate, and the triturated mix powder of dl-α-tocopherol were weighed to reach blend ratios shown in Table 3, and mixed by using a V-blender (5 L) at a rotational frequency of 34 rpm for 10 minutes.

Sieving was performed with a Comil (QC-194S, φ1.143, QUADRO) at 600 rpm to produce a sieved powder.

Subsequently, magnesium stearate was weighed to reach a blend ratio shown in Table 3 and added to the sieved powder, and the resultant was mixed by using a V-blender (5 L) at a rotational frequency of 34 rpm for 7 minutes.
(Tableting)

Molding was performed by using a tablet press (Virgo, KIKUSUI SEISAKUSHO LTD.) at a tableting pressure of approximately 10 kN with setting the tablet mass to 200 mg, providing a plain tablet (containing 2.5% by weight of compound (I) as a weight ratio in terms of the free form to the plain tablet, an oblong tablet, 10.6×5.6 mm).
(Coating)

OPADRY (R) was dispersed in purified water (12.5 w/w %) by using a stirrer (MAZELA Z, TOKYO RIKAKIKAI CO, LTD.) to produce a coating solution.

The plain tablet was coated by using a coater (HI-COATER LABO 30, Freund Corporation) with an air supply temperature of 70° C., an air supply rate of 0.8 m$^3$/min, a spraying rate of approximately 8 g/min, a pan rotation frequency of 20 rpm, and an air exhaust temperature of approximately 60° C. at the end of drying, giving a coated tablet.

(3) Example 12

(Trituration and Mixing)

By using a high-speed mixing granulator (VG-5L, Powrex Corporation), 80.0 g of dl-α-tocopherol and 720.0 g of microcrystalline cellulose were mixed together at an agitator rotation frequency of 280 rpm and a chopper rotation frequency of 3000 rpm for 25 minutes to produce a triturated mix powder of dl-α-tocopherol.
(Mixing/Sieving)

Compound (I), D-mannitol, carmellose calcium, citric acid hydrate, the triturated mix powder of dl-α-tocopherol, and magnesium aluminometasilicate were weighed to reach blend ratios shown in Table 3, and mixed by using a V-blender (2 L) at a rotational frequency of 39 rpm for 10 minutes.

Sieving was performed with a Comil (U-5, φ1.143, QUADRO) at 1560 rpm to produce a sieved powder.

Subsequently, magnesium stearate was weighed to reach a blend ratio shown in Table 3 and added to the sieved powder, and the resultant was mixed by using a V-blender (2 L) at a rotational frequency of 39 rpm for 7 minutes.
(Tableting)

Molding was performed by using a tablet press (Vela2, KIKUSUI SEISAKUSHO LTD.) at a tableting pressure of approximately 9 kN with setting the tablet mass to 100 mg, providing a plain tablet (containing 2.5% by weight of compound (I) as a weight ratio in terms of the free form to the plain tablet, a spherical tablet, 6.5 mm).
(Coating)

OPADRY (R) was dispersed in purified water (12.5 w/w %) by using a stirrer (MAZELA Z, TOKYO RIKAKIKAI CO, LTD.) to produce a coating solution.

The plain tablet was coated by using a coater (HI-COATER FZ20, Freund Corporation) with an air supply temperature of 70° C., an air supply rate of 0.5 m$^3$/min, a spraying rate of approximately 2 g/min, a pan rotation frequency of 20 rpm, and an air exhaust temperature of approximately 54° C. at the end of drying, giving a coated tablet.

(3) Example 13

(Trituration and Mixing)

By using a high-speed mixing granulator (VG-5L, Powrex Corporation), 120.0 g of dl-α-tocopherol and 680.0 g of microcrystalline cellulose were mixed together at an agitator rotation frequency of 280 rpm and a chopper rotation frequency of 3000 rpm for 25 minutes, and 16.23 g of the mix powder obtained and 33.77 g of microcrystalline cellulose were mixed together with a mortar for 5 minutes to produce a triturated mix powder of dl-α-tocopherol.
(Mixing/Sieving)

Compound (I), D-mannitol, carmellose calcium, citric acid hydrate, the triturated mix powder of dl-α-tocopherol, and magnesium aluminometasilicate were weighed to reach blend ratios shown in Table 3, and mixed by using a V-blender (5 L) at a rotational frequency of 34 rpm for 10 minutes.

Sieving was performed with a Comil (U-5, φ1.143, QUADRO) at 1560 rpm to produce a sieved powder.

Subsequently, magnesium stearate was weighed to reach a blend ratio shown in Table 3 and added to the sieved powder, and the resultant was mixed by using a V-blender (5 L) at a rotational frequency of 34 rpm for 7 minutes.

(Tableting)

Molding was performed by using a tablet press (Vela2, KIKUSUI SEISAKUSHO LTD.) at a tableting pressure of approximately 9 kN with setting the tablet mass to 100 mg, providing a plain tablet (containing 2.5% by weight of compound (I) as a weight ratio in terms of the free form to the plain tablet, a spherical tablet, 6.5 mm).

(Coating)

OPADRY (R) was dispersed in purified water (12.5 w/w %) by using a stirrer (MAZELA Z, TOKYO RIKAKIKAI CO, LTD.) to produce a coating solution.

The plain tablet was coated by using a coater (Dria coater 300, Powrex Corporation) with an air supply temperature of 70° C., an air supply rate of 1.2 m$^3$/min, a spraying rate of approximately 7 g/min, a pan rotation frequency of 20 rpm, and an air exhaust temperature of approximately 60° C. at the end of drying, giving a coated tablet.

Evaluation Method and Results

The tablets of Examples 7 to 13 were left to stand under open conditions of 25° C./75% RH/12 weeks, and thereafter main decomposition products were examined through measurement with UHPLC (1290 Infinity, Agilent Technologies) under the above-described analysis conditions. Only the result for Example 12 was obtained under open conditions of 25° C./75% RH/3 months.

Table 4 shows the results (the amounts of decomposition product A and decomposition product B, %). These results demonstrate that the formation ratios of the decomposition products were successfully reduced to values generally equal to or lower than the reference level stated as "Identification Threshold (threshold for requirement of structural identification of impurities): 0.2%" (0.15 or higher and lower than 0.25) in "Revision of Guidelines on Impurities in New Drug Products" (PMSB/ELD Notification No. 0624001, dated Jun. 24, 2003)" by blending dl-α-tocopherol in the range of 0.005 to 0.5% by weight and citric acid hydrate in the range of 1.125 to 2.9% by weight in combination.

TABLE 3

| Components | Composition (% by weight/plain tablet) | | | | | | |
| --- | --- | --- | --- | --- | --- | --- | --- |
| | Example 7 | Example 8 | Example 9 | Example 10 | Example 11 | Example 12 | Example 13 |
| Compound (I) | 4.39 | 4.39 | 4.39 | 4.39 | 4.39 | 4.39 | 4.39 |
| (as the free form) | (2.5) | (2.5) | (2.5) | (2.5) | (2.5) | (2.5) | (2.5) |
| D-Mannitol (Parteck M100, Merck KGaA, Mannogem EZ, SPI Pharma) | 81.31 | 77.83 | 76.61 | 79.11 | 76.61 | 81.31 | 80.69 |
| Carmellose calcium (E.C.G-505, GOTOKU CHEMICAL COMPANY, LTD.) | 10 | 10 | 10 | 10 | 10 | 10 | 10 |
| dl-α-Tocopherol (MITSUBISHI-CHEMICAL FOODS CORPORATION) | 0.1 | 0.3 | 0.1 | 0.2 | 0.5 | 0.005 | 0.075 |
| Citric acid hydrate (Merck KGaA) | 1.5 | 1.9 | 2.9 | 2.8 | 2.5 | 1.5 | 1.125 |
| Microcrystalline cellulose (CEOLUS UF-702, Asahi Kasei Corporation) | 0.9 | 2.5 | 1.2 | 1.7 | 4.5 | 0.995 | 0.925 |
| Carmellose (NS-300, GOTOKU CHEMICAL COMPANY, LTD.) | — | 1.47 | 3.0 | — | — | — | — |
| Magnesium aluminometasilicate (Neusilin UFL2, US2, Fuji Chemical Industries Co., Ltd.) | 0.3 | 0.15 | 0.3 | 0.3 | — | 0.3 | 0.3 |
| Magnesium stearate (common, Taihei Chemical Industrial Co., Ltd.) | 1.5 | 1.5 | 1.5 | 1.5 | 1.5 | 1.5 | 1.5 |
| Total in plain tablet | 100 | 100 | 100 | 100 | 100 | 100 | 100 |
| OPADRY (R) | 5 | 5 | 5 | 5 | 5 | 5 | 5 |
| Total | 105 | 105 | 105 | 105 | 105 | 105 | 105 |

TABLE 4

|  | Example 7 | Example 8 | Example 9 | Example 10 | Example 11 | Example 12 | Example 13 |
|---|---|---|---|---|---|---|---|
| dl-α-Tocopherol (% by weight) | 0.1 | 0.3 | 0.1 | 0.2 | 0.5 | 0.005 | 0.075 |
| Citric acid hydrate (% by weight) | 1.5 | 1.9 | 2.9 | 2.8 | 2.5 | 1.5 | 1.125 |
| Decomposition product A (%) under open conditions of 25° C./75% RH/ 12 weeks | <0.05 | 0.06 | 0.07 | 0.07 | 0.10 | 0.05 | 0.08 |
| Decomposition product B (%) under open conditions of 25° C./75%RH/ 12 weeks | 0.18 | 0.17 | 0.12 | 0.12 | 0.17 | 0.22 | 0.21 |

The invention claimed is:

1. A tablet comprising:

[(1R,5S,6S)-6-(aminomethyl)-3-ethylbicyclo[3.2.0]hept-3-en-6-yl]acetic acid monobenzenesulfonate of formula (I):

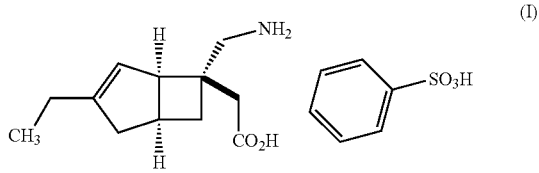

(I)

D-mannitol;
carmellose calcium;
citric acid anhydride or citric acid hydrate, wherein the citric acid anhydride or citric acid hydrate is present at 1.125 to 2.9% by weight of the total weight of the uncoated tablet; and
α-tocopherol, wherein the α-tocopherol is present at 0.005 to 0.5% by weight of the total weight of the uncoated tablet.

2. The tablet of claim 1, wherein the c-tocopherol is present at 0.05 to 0.5% by weight of the total weight of the uncoated tablet.

3. The tablet of claim 1, wherein the compound of formula (I) is present at 1.0 to 5.0% by weight of the total weight of the uncoated tablet.

4. The tablet of claim 1, wherein the average particle size of D-mannitol is 120 μm or smaller, and the D-mannitol is present at 75 to 85% by weight of the total weight of the uncoated tablet.

5. The tablet of claim 1, wherein the carmellose calcium is present at 5 to 15% by weight of the total weight of the uncoated tablet.

6. The tablet of claim 1, further comprising magnesium stearate.

7. The tablet of claim 6, wherein the magnesium stearate is present at 1 to 3% by weight of the total weight of the uncoated tablet.

8. The tablet of claim 1, further comprising magnesium aluminometasilicate and microcrystalline cellulose.

9. The tablet of claim 1, wherein the tablet is a film-coated tablet.

* * * * *